United States Patent [19]

Hirose et al.

[11] 4,354,037

[45] Oct. 12, 1982

[54] PROCESS FOR PREPARING BENZENECARBOXYLIC ACIDS

[75] Inventors: Isao Hirose, Tokyo; Kiyoshi Yamamoto; Hiroyuki Okitsu, both of Iwakuni, all of Japan

[73] Assignee: Teijin Limited, Osaka, Japan

[21] Appl. No.: 346,775

[22] Filed: Feb. 8, 1982

Related U.S. Application Data

[63] Continuation of Ser. No. 164,674, Jun. 30, 1980, abandoned, which is a continuation of Ser. No. 18,030, Mar. 6, 1979, abandoned.

[30] Foreign Application Priority Data

Mar. 7, 1978 [JP] Japan .................................. 53/24932

[51] Int. Cl.$^3$ ............................................. C07C 51/16
[52] U.S. Cl. ................................................ 562/416
[58] Field of Search ............................. 562/412, 416

[56] References Cited

U.S. PATENT DOCUMENTS 3,846,487 11/1974 Shigeyasu et al. ................. 562/416

3,903,148 9/1975 Namie et al. ....................... 562/412

OTHER PUBLICATIONS

Oda, "Unit Process Serial 1: Oxidation", (1963), pp. 58, 59, 77.

Perry, "Chem. E. Handbook", 4th Ed., (1963), pp. 23-13 to 23-15.

*Primary Examiner*—Alan Siegel
*Attorney, Agent, or Firm*—Sherman & Shalloway

[57] ABSTRACT

A process for preparing benzenecarboxylic acids which comprises oxidizing at least one aromatic hydrocarbon selected from the group consisting of p-xylene, p-toluic acid and methyl p-toluate with a molecular oxygen-containing gas in the liquid phase in the substantial absence of a lower aliphatic carboxylic acid as a solvent, said oxidation reaction being carried out in the presence of, as a catalyst, (A) a cobalt compound soluble in the reaction system,
(B) a manganese compound soluble in the reaction system, and
(C) a bromine compound soluble in the reaction system.

18 Claims, No Drawings

PROCESS FOR PREPARING BENZENECARBOXYLIC ACIDS

This is a continuation of application Ser. No. 164,674, filed June 30, 1980, now abandoned, which in turn is a continuation of application Ser. No. 018,030, filed Mar. 6, 1979, now abandoned.

This invention relates to a process for preparing benzenecarboxylic acids which comprises oxidizing at least one aromatic hydrocarbon selected from p-xylene, p-toluic acid and methyl p-toluate with a molecular oxygen-containing gas in the liquid phase in the substantial absence of a lower aliphatic carboxylic acid as a solvent. Particularly, the invention provides a commercial process for preparing terephthalic acid, monomethyl terephthalate or dimethyl terephthalate using the aforesaid aromatic hydrocarbons as a starting material.

Terephthalic acid (sometimes abbreviated "TA" hereinbelow) and dimethyl terephthalate (sometimes abbreviated "DMT" hereinbelow) are useful compounds because the reaction of them with glycols such as ethylene glycol and tetramethylene glycol affords polyester which are commercially required in large quantities as molding materials for fibers, films, etc.

In spite of the numerous methods suggested in the past for the production of TA or DMT, those in actual commercial operation are typified by the following two processes.

One of them is called the Witten-Hercules process which comprises oxidizing p-xylene with a molecular oxygen-containing gas in the liquid phase in the presence of a heavy metal catalyst such as cobalt, manganese or a mixture of both to form p-toluic acid (sometimes abbreviated "PTA" hereinbelow), esterifying PTA with methanol to form methyl p-toluate (sometimes abbreviated "MPT" hereinbelow), oxidizing MPT with a molecular oxygen-containing gas in the liquid phase using cobalt, manganese or a mixture of both as a catalyst to obtain monomethyl terephthalate (sometimes abbreviated "MMT" hereinbelow), and esterifying MMT with methanol to form DMT. This process is described in British Patent Specification No. 727,989.

There is an improvement of this Witten-Hercules process, which comprises oxidizing a mixture of p-xylene and MPT with a molecular oxygen-containing gas in the liquid phase in the presence of the aforesaid heavy metal catalyst, esterifying the resulting oxidation reaction mixture containing PTA and MMT as main ingredients with methanol, separating DMT from the esterified reaction mixture, recycling MPT to the oxidation step, and oxidizing it again together with a fresh supply of p-xylene (see British Patent Specification No. 809,730).

The other is called the Amoco process or SD process. The Amoco process involves oxidizing p-xylene with a molecular oxygen-containing gas in the liquid phase in a lower aliphatic monocarboxylic acid solvent in the presence of a heavy metal catalyst and a bromine compound to form TA directly (see U.S. Pat. No. 2,833,816). The resulting TA can be esterified with methanol, and used as DMT.

The Witten-Hercules process and the Amoco process are practiced on a large scale in the production of DMT and TA, and in recent years, almost all raw materials for polyesters are produced by these two processes. These processes have the following advantages and disadvantages.

Since in the Witten-Hercules process, a lower aliphatic monocarboxylic acid solvent such as acetic acid is not used, and the oxidation conditions are mild, the corrosion of the apparatus is very little although the rate of the reaction is low. Hence, the apparatus can be built by using low-cost stainless steel. This process, however, requires two oxidation steps for the production of DMT from p-xylene, and carbon monoxide, carbon dioxide and high-boiling substances are formed in relatively large quantities. It is extremely difficult therefore to attain a final yield of DMT of more than 90% based on p-xylene in commercial operations.

On the other hand, the Amoco process uses a bromine compound and a lower aliphatic monocarboxylic acid solvent such as acetic acid, and the oxidation is carried out under severe conditions of high temperatures and pressures. Hence, the rate of the reaction is high, and the yield of TA based on p-xylene is as high as 95% or more. However, the reaction apparatus is heavily corroded owing mainly to the use of the bromine compound and the monocarboxylic acid solvent. Thus, ordinary stainless steel cannot be used to build the reaction apparatus, and expensive materials such as Hastelloy or titanium are required. Moreover, even when such an expensive material is used, the apparatus undergoes some corrosion. Furthermore, because the acid solvent is used in a large quantity and the oxidation conditions are severe in the Amoco process, combustion of the solvent itself cannot be avoided, and its loss is not negligible.

It is a first object of this invention to provide a process for preparing benzenecarboxylic acids in high yields which comprises oxidizing at least one aromatic hydrocarbon selected from the group consisting of p-xylene, PTA and MPT with a molecular oxygen-containing gas in the substantial absence of a lower aliphatic monocarboxylic acid.

A second object of this invention is to provide a process for preparing benzenecarboxylic acids at a high rate of reaction with little or no corrosion of the reaction apparatus.

A third object of this invention is to provide a process for preparing benzenecarboxylic acids under mild oxidation conditions in the substantial absence of solvent.

Still other objects and advantages of this invention will become apparent from the following description.

According to this invention, the aforesaid objects and advantages can be achieved by a process for preparing benzenecarboxylic acids by oxidizing at least one aromatic hydrocarbon selected from the group consisting of p-xylene, p-toluic acid (PTA) and methyl p-toluate (MPT) with a molecular oxygen-containing gas in the liquid phase in the substantial absence of a lower aliphatic carboxylic acid as a solvent, said oxidation reaction being carried out in the presence of, as a catalyst, (A) a cobalt compound soluble in the reaction system, (B) a manganese compound soluble in the reaction system, and (C) a bromine compound soluble in the reaction system.

It is well known that heavy metal catalysts such as cobalt, manganese, nickel and chromium are effective as oxidation catalysts in the Witten-Hercules process. Recently, a process was suggested (British Patent Specification No. 1,313,083) in which a mixture of cobalt and manganese is used as a catalyst. This process can afford an effective product composed of PTA and MMT as main ingredients in higher yields. However, even when the oxidation reaction is carried out under preferred conditions using the mixture of cobalt and manganese as a catalyst, the yield of DMT based on p-xylene is at most about 90%, and usually only about 85 to 88%.

A process is also known which involves oxidizing p-xylene with a molecular oxygen-containing gas in the substantial absence of a lower aliphatic carboxylic acid solvent to produce terephthalic acid. In particular, it is known that a mixture of cobalt and manganese is effective as an oxidation catalyst (U.S. Pat. No. 3,883,584). However, the yield of terephthalic acid in this process is not entirely satisfactory, and the rate of reaction is by no means high.

It has now been found in accordance with this invention that by using a combination of (A) a cobalt compound soluble in the reaction system, (B) a manganese compound soluble in the reaction system, and (C) a bromine compound soluble in the reaction system, the desired benzenecarboxylic acids can be prepared in very high yields and at a high rate of reaction without using an aliphatic monocarboxylic acid solvent, and that the reaction can be performed at relatively low temperatures and pressures. If the aforesaid catalyst in accordance with this invention is used as a catalyst in the Witten-Hercules process, the generation of decomposition gases such as carbon monoxide and carbon dioxide by side-reactions is extremely reduced, and it is easy to obtain a yield of DMT of 90% based on p-xylene. Under preferred conditions, the yield reaches 95% or more, and the rate of reaction becomes very high.

It has also been found unexpectedly that the use of the mixture of catalyst components (A), (B) and (C) described above does not substantially corrode the reaction apparatus, and the oxidation reaction can be performed by using the reaction apparatus made of low cost stainless steel.

The work of the present inventors has also shown that when a combination of (A) a cobalt compound soluble in the reaction system, (B) a manganese compound soluble in the reaction system, (C) a bromine compound soluble in the reaction system, and (D) an alkali metal compound soluble in the reaction system, is used as the oxidation catalyst in the process of this invention, operational troubles such as the deposition of cobalt metal on the apparatus can be reduced, the yield of the desired benzenecarboxylic acid somewhat increases, and the corrosion of the apparatus is further reduced, as compared with the case of not using component (D).

The term "reaction system", as used herein in defining the catalyst compounds, denotes an oxidation reaction mixture which contains not only the starting material such as p-xylene, PTA and MPT, but also its oxidation intermediates and the corresponding benzenecarboxylic acid.

The cobalt compound (A) and the manganese compound (B) may be any cobalt and manganese compounds which are at least partly soluble in the reaction system of this invention. Examples of such compound include (1) salts with aliphatic carboxylic acids such as formic acid, acetic acid, propionic acid, butyric acid, caproic acid, stearic acid and palmitic acid, (2) salts with alicyclic carboxylic acids such as naphthenic acid and cyclohexanecarboxylic acid, and (3) salts with aromatic carboxylic acids such as benzoic acid, toluic acid, and naphthalenecarboxylic acid.

The organic carboxylic acids (1), (2) and (3) which form salts with cobalt or manganese preferably have not more than 20 carbon atoms, especially not more than 15 carbon atoms.

Components (A) and (B) can also be used as complexes such as acetylacetonates, methylacetoacetates and ethylacetoacetates. Cobalt and manganese metals, and their inorganic compounds such as the oxides, hydroxides, carbonates and nitrates are by themselves insoluble or only sparingly soluble in the reaction system. However, because as the oxidation reaction proceeds, they form salts with the resulting benzenecarboxylic acids and become soluble in the reaction system, they can also be used as the catalyst without causing any trouble. Cobalt and/or manganese can also be used in the form of bromides. This mode of use is preferred because such bromides simultaneously include the components (A) and/or (B) and component (C). Of the components (A) and (B) described above, the organic carboxylic acid salts (1) to (3) and the bromides are especially preferred.

Examples of the bromine compound (C) soluble in the reaction system are bromine ($Br_2$), hydrogen bromide, ammonium bromide, lithium bromide, sodium bromide, potassium bromide, cobalt bromide, manganese bromide, benzyl bromide, xylyl bromide, aluminum bromide and magnesium bromide. Of these, alkali metal bromides such as lithium bromide, sodium bromide and potassium bromide, and the bromides of cobalt or manganese such as cobalt bromide and manganese bromide are preferred. Such alkali metal bromides can serve both as the components (C) and (D). Cobalt bromide plays a role of both components (A) and (C), and manganese bromide plays a role of both the components (B) and (C). The work of the present inventors shows that preferably, the bromine compound as component (C) is added to the reaction system of this invention such that at least a part, preferably at least 50% by weight, of the bromine compound is in the form of the bromide of a cobalt and/or manganese, and/or the bromide of an alkali metal.

When component (D) is used in the present invention, it is preferably added in the form of an alkali metal bromide.

In the present invention, the alkali metal compound soluble in the reaction system [component (D)] is added if desired. As stated hereinabove, the bromides of alkali metals such as sodium, potassium or lithium, especially sodium or lithium, are especially preferred as the alkali metal compound. Other suitable alkali metal compounds include the hydroxides, the oxides and carbonates of such alkali metals, and salts of these alkali metals with the organic acids mentioned in (1), (2) and (3) above, such as salts with acetic acid, benzoic acid, MMT and PTA.

Among these, the bromides, hydroxides, and acetates of alkali metals, especially sodium or lithium, are preferred. The bromides are especially preferred.

When the reaction in accordance with this invention has proceeded even a little, by-product water is present in the reaction system. The work of the present inventors shows that it is necessary to add the components (C) and (D) to the reaction system in the form of a compound capable of providing a bromine ion and an alkali metal ion in the reaction system of this invention at least containing water. The above-exemplified bromine compounds [component (C)] and the alkali metal compounds [component (D)] can provide a bromine ion and an alkali metal ion in the reaction system of this invention in which at least a small amount of water is present. Compounds which do not provide such ions, such as bromobenzene, m-bromobenzoic acid, and bromonaphthalene do not exhibit an effect as the component (C).

In the process of this invention, at least one aromatic hydrocarbon selected from the group consisting of p-xylene, PTA and MPT is used as a starting material.

In particular, the invention is applicable to
(i) the production of TA from p-xylene or a mixture of p-xylene and PTA,
(ii) the production of TA from PTA,
(iii) the production of MMT from MPT, and
(iv) the production of PTA, MMT and TA from a mixture of p-xylene and MPT. It is especially advantageously applicable to the oxidation of p-xylene or a mixture of it with PTA (i), and the oxidation of a mixture of p-xylene and MPT (iv).

When oxidizing a mixture of p-xylene and MPT (iv), the weight ratio of p-xylene to MPT is preferably from 4:1 to 1:4. By performing the oxidation of the mixture in this ratio, MPT can be recycled to the oxidation step with a good balance after the separation of DMT from the methanol-esterified oxidation reaction mixture, and DMT can be produced in good yields.

According to this invention, benzenecarboxylic acids can be produced in high yields and at a high rate of reaction by causing the cobalt compound (A) and the manganese compound (B) to be present in the reaction system in the following ratios and concentrations calculated as cobalt metal and manganese metal respectively.

(1) The cobalt metal/manganese metal atomic ratio is 99.5/0.5 to 50/50.

(2) The total concentration of cobalt metal and manganese metal in the oxidation reaction system is 150 ppm to 5,000 ppm.

The especially preferred ratios and concentrations of the cobalt compound (A) and the manganese compound (B) in the reaction system of this invention are as follows:

(1) The cobalt metal/manganese metal atomic ratio is 99.3/0.7 to 60/40.

(2) The total concentration of the cobalt metal and the manganese metal in the oxidation reaction system is from 200 ppm to 3,000 ppm.

If the amount of the manganese metal is smaller than that defined by the cobalt metal/manganese metal atomic ratio of 99.5/0.5, the advantage of using the cobalt compound (A) in combination with the manganese compound (B) is reduced, and the amounts of by-products such as carbon monoxide and carbon dioxide increase and the yields of the benzenecarboxylic acids decrease. On the other hand, if the amount of the manganese metal increases beyond the cobalt metal/manganese metal atomic ratio of 50/50, the yields of the benzenecarboxylic acids tend to decrease. When the cobalt metal/manganese metal atomic ratio is from 99.3/0.7 to 60/40, side-reactions are reduced, and the benzenecarboxylic acids can be obtained in higher yields. Thus, in the oxidation catalyst used in this invention, very great effects can be obtained by combining a relatively small amount of the manganese compound (B) with the compound (A). The amounts of the by-products are minimized, and the yields of the benzenecarboxylic acids are maximized, when the cobalt metal/manganese metal atomic ratio is from 99.2/0.8 to 70/30.

On the other hand, the total concentration of the cobalt compound (A) and the manganese compound (B) as cobalt metal and the manganese metal in the reaction system affect the yields of the benzenecarboxylic acids and the rate of reaction. Preferably, these compounds (A) and (B) are used such that the total concentration of the cobalt metal and the manganese metal is from 150 ppm to 5,000 ppm, especially from 200 ppm to 3,000 ppm. If the total concentration of the cobalt metal and the manganese metal is less than 200 ppm, especially less than 150 ppm, the amounts of by-products such as carbon monoxide and carbon dioxide increase, and the yields of the desired benzenecarboxylic acids and the rate of reaction decrease.

When the total concentration of the cobalt metal and the manganese metal is at least 150 ppm, the rate of reaction increases with increasing total concentration of these metals, and the proportion of the by-products decreases accordingly. When the total concentration of these metals is at least 200 ppm, especially at least 250 ppm, the yields of the benzenecarboxylic acids increase, and the rate of reaction become very high. Hence, this total concentration range is very advantageous in commercial practice.

When the total concentration of the cobalt metal and the manganese metal exceeds 3,000 ppm, especially 5,000 ppm, the rate of reaction decreases gradually. With increasing total concentration, the amounts of by-products such as carbon monoxide and carbon dioxide increase relatively slowly, but not to a great extent. However, the use of much cobalt metal and manganese metal in a total amount exceeding 5,000 ppm does not bring about any corresponding advantage, and the reaction operation and the recovery of the catalyst become troublesome. The upper limit of the total concentration is therefore automatically set in view of these factors. Accordingly, the sufficient total concentration of the cobalt and manganese metals is 3,000 ppm or below from the commercial standpoint.

The bromine compound (C) is caused to be present preferably in the following ratio and concentration calculated as bromine.

(1) The bromine/(cobalt metal+manganese metal) atomic ratio does not exceed 2/1.

(2) The total concentration of bromine in the oxidation reaction system does not exceed 3,000 ppm.

This makes it possible to decrease the amount of by-products such as carbon monoxide and carbon dioxide, increase the selectivity for the intended benzenecarboxylic acid, and to increase the rate of reaction. Even when the bromine compound (C) is added in a very small amount, the above effects are noted according to the amount added. Hence, the amount of the bromine compound (C) may small. When bromine is used in an amount exceeding that determined by a bromine/(cobalt metal+manganese metal) atomic ratio of more than 2, the generation of carbon monoxide and carbon dioxide by side-reactions increases, and the yield of the benzenecarboxylic acid decreases.

The suitable concentration of the bromine compound (C) in the oxidation reaction system is not more than 3,000 ppm, preferably not more than 2,500 ppm, calculated as bromine. Even when the bromine concentration exceeds this upper limit, the yield of the benzenecarboxylic acid does not decrease particularly drastically, nor is the rate of reaction lowered abruptly. However, the use of the bromine compound in such a large amount does not bring about an appreciable advantage, but rather is uneconomical. Advantageously, therefore, the proportion and concentration of the bromine compound (C) as bromine should be as follows:

(3') The bromine/(cobalt metal+manganese metal) atomic ratio does not exceed 1.5/1, and (4') The concentration of bromine in the oxidation reaction system is within the range of 50 ppm to 2,500 ppm, especially from 70 ppm to 1,500 ppm.

Thus, according to this invention, benzenecarboxylic acids can be produced in very high yields at a high rate of reaction by performing the oxidation reaction such that the proportions and concentrations of the catalyst ingredients (A) to (C) are set within the above-described ranges. Moreover, this brings about the advantage of surprisingly reducing the corrosion of the reaction apparatus by the bromine compound (C).

One characteristic feature of the catalyst of this invention is that the catalyst exhibits superior activity not only when the total concentration of the cobalt compound (A) and the manganese compound (B) is relatively low, but also when it is considerably high.

For example, Table 9 of German OLS No. 2144920 shows that in the oxidation of a mixture of p-xylene and MPT by the Witten-Hercules process using a cobalt compound and a manganese compound as a catalyst, effective carboxylic acids such as PTA and MMT can be obtained in the highest yield when the total concentration of these compounds as cobalt metal and manganese metal is about 100 to about 500 ppm, especially about 230 ppm. If the total concentration increases further, the yield of the effective carboxylic acids tends to decrease gradually.

According to Table 5 of U.S. Pat. No. 3,883,584, when TA is produced by oxidizing p-xylene using a cobalt compound and a manganese compound as a catalyst, the catalyst exhibits the best catalytic activity when the total concentration of these compounds as cobalt metal and manganese metal is about 80 ppm to about 420 ppm, especially about 170 ppm, and the activity of the catalyst decreases when the total concentration increases further.

In contrast, according to this invention, when the total concentration of the cobalt metal and manganese metal in the oxidation reaction is at least 150 ppm, preferably at least 200 ppm, the yields of the benzenecarboxylic acids and the rate of reaction increase. When the total concentration is as high as about 500 ppm, about 700 ppm, or about 1,000 ppm, the desired benzenecarboxylic acids can be produced in higher yields and at higher rates of reaction. It is especially surprising that according to this invention, even when the total concentration of the cobalt metal and manganese metal is as high as about 2,500 ppm, the yields of the benzenecarboxylic acids and the rate of reaction are extremely high.

Thus, the present invention achieves the excellent advantage that benzenecarboxylic acids can be produced at high rates of reaction and in very high yields even when the total concentration of the cobalt metal and manganese metal is as high as is unsuitable in the prior art.

In another embodiment of this invention, the oxidation reaction can be performed in the further presence of an alkali metal compound soluble in the reaction system (D) in addition to the components (A), (B) and (C). By causing the alkali metal compound (D) to be present in the oxidation reaction system in a total alkali metal concentration of not more than 2,500 ppm, preferably 5 ppm to 1,500 ppm, the amounts of by-products such as carbon monoxide and carbon dioxide decrease slightly and the yields of the benzenecarboxylic acids somewhat increase over the case of not using the component (D). Furthermore, the presence of the alkali metal compound (D) is effective for preventing the deposition of cobalt and manganese metals, especially the former, attributed to the metallic compounds (A) and (B), and serves to further inhibit the corrosion of the reaction apparatus by the bromine compound (C).

As stated hereinabove, the present invention produces an excellent result even when the total concentration of the cobalt metal and manganese metal in the oxidation reaction system is relatively low. In particular, it brings about the unique phenomenon that when the concentration of these metals is relatively high, the activity of the catalyst does not decrease, but rather increases. When the oxidation reaction of this invention is performed while the total concentration of the cobalt metal and manganese metal is relatively high, cobalt and/or manganese metal, especially the cobalt metal, deposits on the reaction apparatus, and causes the reduction of thermal conduction and the clogging of various supply openings and discharge openings, etc., thus hampering the stable operation. Deposition of the metal does not always occur in such a high concentration, and the degree of the deposition of the metals is affected by the oxidation conditions such as the proportions of the catalyst ingredients, the reaction temperature and the composition of the oxidation reaction mixture.

The alkali metal compound (D) in the catalyst of this invention is seen to produce an effect of inhibiting the deposition of the cobalt metal and/or manganese metal on the oxidation reaction apparatus. It is especially preferred that the alkali metal compound (D) should be present in the oxidation reaction system in a concentration of 7 ppm to 1,000 ppm calculated as the alkali metal.

The use of the alkali metal compound (D) is commercially advantageous because, as described hereinabove, the yields of the benzenecarboxylic acids and the rate of reaction increase somewhat over the case of not using the component (D), and the oxidation reaction can be stably performed over a long period of time.

In still another embodiment of this invention, a part of the cobalt compound (A) can be replaced by a nickel compound which is soluble in the reaction system. The use of nickel compound in this manner does not particularly increase the yields of the benzenecarboxylic acids or the rate of the oxidation reaction. However, the oxidation reaction can be performed without any serious trouble even if the cobalt compound (A) is partly replaced by a nickel compound containing not more than 50%, preferably not more than 20%, of nickel metal in terms of the atomic ratio of nickel to cobalt.

Preferably, the oxidation reaction in accordance with this invention is performed at a temperature of 150° to 220° C., especially 160° to 210° C. If the reaction temperature is lower than 150° C., the rate of the reaction is slow, and it is disadvantageous for the commercial production of benzenecarboxylic acids. On the other hand, if the reaction temperature exceeds 220° C., the yields of the desired benzenecarboxylic acids gradually decrease.

The process of this invention can be performed very advantageously at a temperature of at least 160° C., because the yields of the benzenecarboxylic acids are high, and the rate of reaction is also high. In particular, the process of this invention is characterized by the fact that the yields of the benzenecarboxylic acids are very high and the rate of reaction is also high, at a reaction temperature of as high as 180° to 210° C.

Since the oxidation reaction of this invention is performed in the liquid phase, the reaction pressure may be the one which is sufficient to maintain the oxidation reaction system in the liquid phase. Usually, the reaction pressure is atmospheric pressure to 50 kg/cm$^2$. The upper limit of the reaction pressure is desirably set so that water formed as a result of the reaction does not build up in the reaction system. Advantageously, the partial pressure of oxygen is set within the range of 0.2 kg/cm$^2$ to 10 kg/cm$^2$, especially within the range of 0.4 kg/cm$^2$ to 5 kg/cm$^2$.

Not only pure oxygen but also a mixture of oxygen with an inert gas such as nitrogen or carbon dioxide is used as the molecular oxygen-containing gas which acts as an oxidizer. Air is the least expensive and is available easily.

In the process of this invention, it is not necessary to use an aliphatic carboxylic acid solvent such as acetic acid as in the conventional Amoco process, nor is it intrinsically necessary to use a diluent or solvent such as benzene, benzoic acid or methyl benzoate.

The oxidation reaction of this invention can be performed either batchwise or continuously. When oxidation towers are used, a single oxidation tower or a plurality of oxidation towers connected in series can be used.

By performing the oxidation reaction in the manner described hereinabove, the oxidation reaction mixture containing benzenecarboxylic acids corresponding to the starting materials can be obtained. As required, the desired benzenecarboxylic acids are recovered from the oxidation reaction mixture either as such or as carboxylates after esterification with methanol. The oxidation reaction mixture contains as main ingredients p-toluic acid, monomethyl terephthalate, terephthalic acid, or mixtures thereof, and also oxidation intermediates and by-products, although the proportions of these ingredients vary according to the starting material used. The method of after-treating the oxidation reaction mixture differs depending upon whether the desired product is terephthalic acid or dimethyl terephthalate. The method of after-treatment will be briefly described below with reference to some specific examples.

When p-xylene or a mixture of p-xylene and PTA is to be oxidized, it is advantageous to perform the oxidation reaction such that the content of the resulting terephthalic acid in the oxidation reaction mixture does not exceed 60% by weight, preferably 45% by weight, based on the total weight of the reaction mixture. Because terephthalic acid is solid, if the oxidation reaction mixture contains more than 45% by weight, especially more than 60% by weight, of terephthalic acid, the oxidation reaction will be slurried, and the oxidation reaction will be difficult to perform smoothly. The oxidation reaction mixture obtained by oxidizing p-xylene or a mixture of it with PTA contains high-boiling by-products and oxidation intermediates such as p-tolualdehyde, p-formylbenzaldehyde and p-methylbenzyl alcohol, and the unreacted p-xylene or PTA, in addition to terephthalic acid as the desired product.

Accordingly, the crude terephthalic acid is separated from the oxidation reaction mixture by solid-liquid separation, and if desired, then purified. In the meantime, the oxidation reaction mixture left after the separation of the crude terephthalic acid is recycled to the oxidation step. The separated terephthalic acid can be used directly as a material for polyesters, and if required, it can be esterified with methanol to form DMT.

When the process of oxidation in accordance with this invention is applied to a mixture of p-xylene and MPT, the resulting oxidation reaction mixture contains oxidation intermediates and by-products in addition to PTA, MMT and TA. The reaction mixture is directly esterified with methanol, and DMT is separated from the esterified reaction mixture by distillation. In the meantime, MPT, etc., as intermediates, of DMT, are recycled and used again as a raw material in the oxidation reaction of this invention. The method for esterification and the method for separating and recovering DMT are well known as the Witten-Hercules process, and are described in detail in British Patent Specifications Nos. 809,730 and 1,313,083, for example.

In the production of DMT by the Witten-Hercules process, the present invention can be advantageously applied to the oxidation step of this process, as stated hereinabove. The catalyst used in the oxidation reaction which consists of the components (A), (B) and (C) and optionally component (D) may be sent to the subsequent esterification step without separation from the oxidation reaction mixture. If desired, the catalyst is separated from the oxidation reaction mixture either wholly or partly, and the residue is subjected to the subsequent esterification step.

When the oxidation reaction mixture obtained by the Witten-Hercules process is heated at a temperature of at least 220° C. without subsequent esterification, terephthalic acid will be formed in an amount larger than that of the TA initially contained in the oxidation reaction mixture. The process for producing terephthalic acid by such a procedure is described in U.S. Pat. No. 3,513,193. Moreover, the oxidation process of the present invention can be utilized effectively to oxidize such a mixture of p-xylene and MPT, and to produce terephthalic acid from the resulting oxidation reaction mixture. The preferred temperature for heating the oxidation reaction mixture in this process is 230° to 280° C., and the preferred period of time during which the oxidation reaction mixture is maintained at an elevated temperature is 5 minutes to 10 hours, especially 30 minutes to 6 hours. The resulting terephthalic acid can be separated and recovered, for example, by a solid-liquid separating technique.

By oxidizing the specified aromatic hydrocarbon in the presence of the components (A), (B) and (C) and optionally the component (D) as a catalyst without using a lower aliphatic carboxylic acid solvent such as acetic acid, the desired benzenecarboxylic acids can be produced in surprisingly high yields with a great reduction in the amounts of by-products such as carbon monoxide and carbon dioxide at a very high rate of reaction. The industrial value of the process of this invention is outstanding.

The invention has the further advantage that corrosion of an apparatus made of stainless steel or the like, which is frequently observed in a process involving the use of a bromine compound, scarcely occurs, and it is not necessary to build the apparatus using expensive materials such as Hastelloy or titanium.

The following Examples and Comparative Examples illustrate the process of this invention more specifically. It should be understood however that the invention is in no way limited to these examples.

EXAMPLES 1 TO 7 AND COMPARATIVE EXAMPLES 1 AND 2

A 500 cc. titanium autoclave equipped with a reflux condenser, stirrer and gas blow inlet was charged with 60 g of p-xylene (PX for short), 140 g of MPT, 5 g of PTA, cobalt acetate, manganese acetate and lithium bromide. The mixture was stirred at high speed at a temperature of 170° C. and a pressure of 5 kg/cm$^2$·G, and air was blown into the autoclave so that the flow rate of the exhaust gas from the outlet became 1,000 cc/min (atmospheric pressure). The starting mixture was thus reacted for 3 hours after the absorption of oxygen began.

After the reaction, the reaction mixture was cooled, and analyzed to determine the amounts of the constituents. The yield of effective products (PTA, MMT, TA, p-methylbenzyl alcohol, p-methoxycarbonylbenzyl alcohol, benzyl benzoate-type compounds having these compounds as acid and alcohol components, compounds convertible to DMT by oxidation and/or esterification, such as p-tolualdehyde, p-formylbenzoic acid and its methyl ester) as intermediates for production of DMT was calculated in accordance with the following equation.

$$\text{Yield of effective products (mole \%)} = \frac{\text{Moles of the effective products formed}}{\text{Moles of } PX \text{ and moles of } MPT \text{ consumed}} \times 100$$

Carbon dioxide and carbon monoxide in the exhaust gas were analyzed, and the combustion ratio by the oxidation reaction of this invention was calculated in accordance with the following equation.

$$\text{Combustion ratio} = \frac{\text{Total amount (mmoles) of CO and CO}_2 \text{ formed}}{\text{Weight (g) of the product} \times \text{Acid value (mg KOH/g) of the product}} \times 56.1 \times 100$$

The combustion ratio is the amount (moles) of carbon monoxide and carbon dioxide formed per 100 cc of the resulting carboxylic acid.

Furthermore, to compare the rates of formation of the effective oxidation products such as PTA, MMT and TA, the acid value of the oxidation product was measured by alkali titration, and divided by the reaction time, thereby obtaining the rate of increase of the acid value per hour.

The amounts of cobalt acetate, manganese acetate, and lithium bromide used in the above oxidation experiment were such that the atomic ratio of Co:Mn:Br was maintained constant at 1:0.21:1, and the total amount of these components were varied.

The results are shown in Table 1.

For comparison, Examples 1 and 5 were repeated except that lithium bromide was not added (Comparative Examples 1 and 2). The results are also shown in Table 1.

TABLE 1

| Run No. | Amounts of catalysts (mg-atom) Co | Mn | Br | Concentrations of the catalyst ingredients in the starting mixture (ppm) Co | Mn | Br | Yield of the effective products (mole %) | Combustion ratio | Increase of acid value per hour (mg KOH/g·hr) | Final acid value (mg KOH/g) | Content of TA (wt. %) |
|---|---|---|---|---|---|---|---|---|---|---|---|
| Example 1 | 0.28 | 0.06 | 0.28 | 80 | 16 | 108 | 71.3 | 19.2 | 69 | 208 | 7.1 |
| Example 2 | 0.70 | 0.15 | 0.69 | 200 | 40 | 270 | 93.8 | 13.8 | 73 | 220 | 8.0 |
| Example 3 | 1.39 | 0.30 | 1.39 | 400 | 80 | 540 | 96.0 | 7.9 | 82 | 245 | 10.5 |
| Example 4 | 2.09 | 0.45 | 2.08 | 600 | 120 | 810 | 97.4 | 4.5 | 84 | 251 | 11.1 |
| Example 5 | 2.78 | 0.60 | 2.77 | 800 | 160 | 1080 | 97.8 | 3.3 | 84 | 253 | 11.2 |
| Example 6 | 6.96 | 1.49 | 6.93 | 2000 | 400 | 2700 | 97.6 | 3.6 | 85 | 255 | 11.2 |
| Example 7 | 10.44 | 2.24 | 10.39 | 3000 | 600 | 4050 | 97.2 | 4.2 | 73 | 219 | 8.1 |
| Comparative Example 1 | 0.28 | 0.06 | 0 | 80 | 16 | 0 | 91.0 | 20.5 | 68 | 205 | 6.3 |
| Comparative Example 2 | 2.78 | 0.60 | 0 | 800 | 160 | 0 | 90.2 | 24.6 | 67 | 200 | 6.1 |

Each of the oxidation products obtained in Example 5 and Comparative Example 2 was charged into a 500 cc titanium autoclave equipped with a reflux condenser, stirrer, gas inlet and methanol inlet. The mixture was stirred at high speed at a temperature of 270° C. and a pressure of 25 kg/cm$^2$·G in an atmosphere of nitrogen, and methanol was introduced at a rate of 100 cc per hour. Nitrogen gas was blown into the autoclave so that its flow rate at the outlet became 400 cc/min. The reaction was performed for 3 hours. During the reaction, a condensed liquid consisting mainly of the excess of methanol resulting from cooling by the reflux condenser was withdrawn successively out of the reaction system. Low-boiling components such as methanol and water were driven off by heating and the remaining condensed components were analyzed for chemical composition together with the esterification product recovered from the autoclave after the reaction. Table 2 summarizes the acid value of the esterification product and the proportions of the main products.

TABLE 2

| Run No. | Acid value of the esterification product (mg KOH/g) | Proportion (wt. %) of the main products MPT | DMT |
|---|---|---|---|
| Example 5 | 3 | 49.0 | 42.3 |
| Comparative Example 2 | 3 | 62.5 | 30.1 |

EXAMPLES 8 TO 14 AND COMPARATIVE EXAMPLES 3 AND 4

The same type of autoclave as in Examples 1 to 7 was charged with 60 g of PX, 140 g of MPT, 5 g of PTA, 0.206 g (2 mg-atom; 771 ppm as Br in the starting mixture fed) of sodium bromide, and 2 mmoles in total of cobalt acetate tetrahydrate and manganese acetate tetrahydrate (with varying ratios between the cobalt and manganese compounds). The mixture was stirred at high speed at a temperature of 170° C. and a pressure of 5 kg/cm²·G. Air was blown into the autoclave so that the flow rate of the exhaust gas became 1,000 cc/min. (atmospheric pressure), and PX, MPT and PTA were reacted for 3 hours. The yield of the effective products, the combustion ratio and the acid value were measured in the same way as in Examples 1 to 7, and the results are shown in Table 3.

manganese acetate tetrahydrate and varying amounts of lithium bromide. The mixture was stirred at high speed at a temperature of 165° C. and 5 kg/cm²·G. Air was blown into the autoclave so that the flow rate of the exhaust gas became 1,000 cc/min. (atmospheric pressure). Thus, the starting mixture was reacted for 3 hours.

In the same way as in Examples 1 to 7, the yield of the effective products, the combustion ratio, and the rate of increase of the acid value per hour were measured. The results are shown in Table 4 together with those of Comparative Example 5 in which lithium bromide was not added.

TABLE 4

| Run No. | Amount of LiBr LiBr (mmoles) | Amount of LiBr Br (ppm) in the starting mixture | Br/heavy metal ratio (atomic ratio) | Yield of the effective products (mole %) | Combustion ratio | Increase of acid value per hour (mg KOH/g.hr) | Final acid value (mg KOH/g) | Content of TA (wt. %) |
|---|---|---|---|---|---|---|---|---|
| Example 15 | 0.08 | 30 | 0.02 | 91.0 | 26.0 | 63 | 189 | 5.6 |
| Example 16 | 0.18 | 70 | 0.05 | 91.7 | 18.1 | 64 | 193 | 5.8 |
| Example 17 | 0.69 | 270 | 0.20 | 94.2 | 12.5 | 67 | 202 | 6.1 |
| Example 18 | 1.39 | 540 | 0.41 | 96.3 | 6.1 | 77 | 230 | 8.6 |
| Example 19 | 4.16 | 1620 | 1.23 | 97.7 | 3.5 | 81 | 242 | 9.9 |
| Example 20 | 25.66 | 10000 | 7.59 | 96.1 | 7.8 | 68 | 205 | 6.4 |
| Comparative Example 5 | 0 | 0 | 0 | 90.1 | 24.5 | 60 | 180 | 4.8 |

EXAMPLES 21 TO 23

The procedure of Examples 15 to 20 was repeated except that the amount of cobalt acetate tetrahydrate was changed to 0.483 g (1.94 mmoles; 557 ppm as Co in

TABLE 3

| Run No. | Amounts of heavy metals added (mg-atom) Co | Amounts of heavy metals added (mg-atom) Mn | Co/Mn atomic ratio | Concentration of heavy metals (ppm) Co | Concentration of heavy metals (ppm) Mn | Yield of the effective products (mole %) | Combustion ratio | Increase of acid value per hour (mg KOH/g.hr) | Final acid value (mg KOH/g) | Content of TA (wt. %) |
|---|---|---|---|---|---|---|---|---|---|---|
| Comparative Example 3 | 2.0 | 0 | 100/0 | 575 | 0 | 92.1 | 17.8 | 87 | 260 | 11.2 |
| Example 8 | 1.996 | 0.004 | 99.8/0.2 | 573 | 1.1 | 92.2 | 17.6 | 85 | 254 | 11.0 |
| Example 9 | 1.994 | 0.006 | 99.7/0.3 | 573 | 1.6 | 92.3 | 17.6 | 84 | 253 | 11.0 |
| Example 10 | 1.98 | 0.02 | 99/1 | 569 | 5.4 | 96.5 | 6.3 | 83 | 249 | 10.7 |
| Example 11 | 1.8 | 0.2 | 90/10 | 517 | 54 | 97.0 | 5.1 | 83 | 249 | 10.8 |
| Example 12 | 1.65 | 0.35 | 82.5/17.5 | 474 | 94 | 96.4 | 6.8 | 81 | 243 | 10.1 |
| Example 13 | 1.0 | 1.0 | 50/50 | 287 | 268 | 94.4 | 13.8 | 71 | 212 | 6.9 |
| Example 14 | 0.4 | 1.6 | 20/80 | 115 | 428 | 92.4 | 20.5 | 68 | 203 | 6.0 |
| Comparative Example 4 | 0 | 2.0 | 0/100 | 0 | 536 | 89.7 | 27.1 | 56 | 169 | 4.3 |

EXAMPLES 15 TO 20 AND COMPARATIVE EXAMPLE 5

The same autoclave as used in Examples 1 to 7 was charged with 60 g of PX, 140 g of MPT, 5 g of PTA, 0.692 g (2.78 mmoles; 800 ppm as Co in the starting mixture fed) of cobalt acetate tetrahydrate, 0.147 g (0.60 mmole; 160 ppm as Mn in the starting mixture fed) of the starting mixture fed), the amount of manganese acetate tetrahydrate was changed to 0.015 g (0.06 mmole; 16 ppm as Mn in the starting mixture fed), and sodium bromide was used instead of lithium bromide in the amounts shown in Table 5, and the reaction was performed at 180° C. and 15 kg/cm²·G for 2 hours. The results are shown in Table 5.

TABLE 5

| Run No. | Amount of sodium bromide NaBr (mmoles) | Amount of sodium bromide Br (ppm) in the starting mixture | Br/heavy metal ratio (atomic ratio) | Combustion ratio | Increase of acid value per hour (mg KOH/g.hr) | Final acid value (mg KOH/g) |
|---|---|---|---|---|---|---|
| Example 21 | 0.13 | 50 | 0.07 | 19.4 | 88 | 176 |
| Example 22 | 0.77 | 300 | 0.39 | 12.8 | 92 | 184 |
| Example 23 | 1.54 | 600 | 0.77 | 7.3 | 90 | 180 |

EXAMPLES 24 TO 30

The same titanium autoclave as used in Examples 1 to 7 was charged with 60 g of PX, 140 g of MPT, 5 g of PTA, 0.692 g (2.78 mmoles; 800 ppm of Co in the starting mixture fed) of cobalt acetate tetrahydrate, 0.147 g (0.60 mmole; 160 ppm as Mn in the starting mixture fed) of manganese acetate tetrahydrate, and 0.260 g (2.53 mmoles; 1,000 ppm as Br in the starting mixture fed) of sodium bromide. Air was blown into the autoclave so that the flow rate of the exhaust gas became 1,000 cc/min. (atmospheric pressure). The reaction pressure was set at 15 kg/cm$^2$·G, and PX, MPT and PTA were oxidized at the temperatures and for the periods of time shown in Table 6. The Co:Mn:Br atomic ratio in the starting mixture was 1:0.22:0.91.

In the same way as in Examples 1 to 7, the yield of the effective products, the combustion ratio and the rate of increase of the acid value per hour were measured, and the results are shown in Table 6.

TABLE 6

| Run No. | Reaction temperature (°C.) | Reaction time (hours) | Yield of the effective products (mole %) | Combustion ratio | Increase of acid value per hour (mg KOH/g·hr) | Final acid value (mg KOH/g) | Content of TA (wt. %) |
|---|---|---|---|---|---|---|---|
| Example 24 | 140 | 4 | 95.3 | 13.0 | 38 | 152 | 3.2 |
| Example 25 | 150 | 3 | 96.8 | 5.6 | 73 | 219 | 8.1 |
| Example 26 | 160 | 2.5 | 97.9 | 3.5 | 89 | 222 | 8.5 |
| Example 27 | 180 | 2 | 97.9 | 3.4 | 94 | 188 | 5.2 |
| Example 28 | 200 | 2 | 97.5 | 3.1 | 100 | 199 | 5.9 |
| Example 29 | 210 | 2 | 96.9 | 3.5 | 109 | 218 | 8.3 |
| Example 30 | 220 | 2 | 96.4 | 4.2 | 104 | 207 | 6.7 |

EXAMPLES 31 AND 32

The procedure of Examples 24 to 30 was repeated using 0.483 g (1.94 mmoles; 557 ppm as Co in the starting mixture fed) of cobalt acetate tetrahydrate, 0.015 g (0.06 mmole; 16 ppm as Mn in the starting mixture fed) of manganese acetate tetrahydrate, and 0.079 g (0.77 mmole; 300 ppm as Br in the starting mixture fed) of sodium bromide. Thus, the effect of the reaction temperature was examined. The results are shown in Table 7.

TABLE 7

| Run No. | Reaction temperature (°C.) | Reaction time (hours) | Combustion ratio | Increase of acid value per hour (mg KOH/g·hr) | Final acid value (mg KOH/g) | Content of TA (wt. %) |
|---|---|---|---|---|---|---|
| Example 31 | 150 | 3 | 15.7 | 69 | 208 | 6.6 |
| Example 22 | 180 | 2 | 12.8 | 92 | 184 | 5.1 |
| Example 32 | 210 | 2 | 19.0 | 106 | 211 | 7.7 |

EXAMPLES 33 TO 37 AND COMPARATIVE EXAMPLE 6

The same titanium autoclave as used in Examples 1 to 7 was charged with 70 g of PX, 130 g of MPT and 5 g of PTA, and also with cobalt acetate tetrahydrate, manganese acetate tetrahydrate and each of the bromine compounds indicated in Table 8 in amounts corresponding to Co, Mn and Br concentrations of 800 ppm, 160 ppm, and 1080 ppm, respectively. The mixture was stirred at high speed at a temperature of 165° C. and a pressure of 5 kg/cm$^2$·G. Air was blown into the autoclave so that the flow rate of the exhaust gas from the outlet became 1000 cc/min. (atmospheric pressure), and PX, MPT and PTA were reacted for 3 hours.

In the same way as in Examples 1 to 7, the yield of the effective products, the combustion ratio and the rate of increase of the acid value per hour were measured, and the results are shown in Table 8.

In Comparative Example 6, m-bromobenzoic acid incapable of generating a bromine ion easily was used as the bromine compound.

TABLE 8

| Run No. | Bromine compound | Yield of the effective products (mole %) | Combustion ratio | Increase of acid value per hour (mg KOH/g·hr) | Final acid value (mg KOH/g) |
|---|---|---|---|---|---|
| Example 33 | Cobalt bromide hexahydrate | 97.6 | 3.8 | 73 | 218 |
| Example 34 | Sodium bromide | 97.9 | 3.2 | 78 | 234 |
| Example 35 | Potassium bromide | 97.7 | 3.7 | 77 | 232 |
| Example 36 | Ammonium bromide | 97.5 | 3.8 | 77 | 230 |
| Example 37 | Benzyl bromide | 97.7 | 3.4 | 75 | 225 |
| Comparative Example 6 | m—Bromobenzoic acid | 92.1 | 17.3 | 63 | 188 |

EXAMPLES 38 TO 40

The same autoclave as used in Examples 1 to 7 was charged with 60 g of PX, 140 g of MPT and 5 g of PTA, 0.015 g (0.06 mmole; 16 ppm as Mn in the starting mixture fed) of manganese acetate tetrahydrate, 1.94 mmoles in total of cobalt acetate tetrahydrate and nickel acetate tetrahydrate, and 0.158 g (1.54 mmoles; 600 ppm as Br in the starting mixture fed) of sodium bromide. Air was blown into the autoclave so that the flow rate of the exhaust gas became 1000 cc/min. (atmospheric pressure). With stirring at high speed, PX, MPT and PTA were reacted at a temperature of 180° C. and a pressure of 15 kg/cm$^2$·G for 2 hours.

In the same way as in Examples 1 to 7, the yield of the effective products, the combustion ratio, and the rate of increase of the acid value per hour were measured, and the results are shown in Table 9.

TABLE 9

| Run No. | Amount of Co added mg-atom | Amount of Co added ppm | Amount of Ni added mg-atom | Amount of Ni added ppm | Yield of the effective products (mole %) | Combustion ratio | Increase of acid value per hour (mg KOH/g.hr) | Final acid value (mg KOH/g) | Content of TA (wt. %) |
|---|---|---|---|---|---|---|---|---|---|
| Example 23 | 1.94 | 557 | 0 | 0 | 96.2 | 7.3 | 90 | 180 | 5.0 |
| Example 38 | 1.90 | 546 | 0.04 | 11 | 96.0 | 7.7 | 90 | 179 | 4.7 |
| Example 39 | 1.745 | 501 | 0.194 | 56 | 95.4 | 9.1 | 88 | 176 | 4.4 |
| Example 40 | 0.97 | 279 | 0.97 | 278 | 90.3 | 23.5 | 81 | 161 | 3.5 |

EXAMPLE 41

The same autoclave as used in Examples 1 to 7 was charged with 60 g of PX, 140 g of MPT, 5 g of PTA, 0.373 g (1.5 mmoles) of cobalt acetate tetrahydrate, 0.073 g (0.3 mmole) of manganese acetate tetrahydrate, and 0, 2.4 or 15 mmoles of lithium acetate. The Co:Mn:Br atomic ratio was constant at 1:0.1:1, and the Li/Br atomic ratio was maintained at 0, 0.8 and 5.0, respectively. Air was blown into the autoclave so that the flow rate of the exhaust gas at the outlet was 1,000 cc/min. PX, MPT and PTA were reacted for 3 hours at a temperature of 170° C. and a pressure of 5 kg/cm$^2$·G. By the addition of lithium acetate, the rate of increase of the acid value per hour increased by about 15%, but scarcely any change was observed in the combustion ratio.

EXAMPLES 42 AND 43 AND COMPARATIVE EXAMPLE 7

The same autoclave as used in Examples 1 to 7 was charged with 200 g of PX, 5 g of PTA, 2.7 mg-atoms (776 ppm as Co in the starting mixture fed) of cobalt, 0.073 g (0.3 mmole; 80 ppm as Mn in the starting mixture fed) of manganese acetate tetrahydrate, and 3 mg-atoms (1170 ppm as Br in the starting mixture fed) of Br. As Co and Br, cobalt acetate tetrahydrate, cobalt bromide hexahydrate and the lithium bromide were used in the proportions shown in Table 10. Air was blown into the autoclave so that the flow rate of the exhaust gas at the outlet was 1,000 cc/min (atmospheric pressure). With stirring at high speed, PX and PTA were reacted for 3 hours at a temperature of 180° C. and a pressure of 5 kg/cm$^2$·G.

In the same way as in Examples 1 to 7, the combustion ratio and the rate of increase of the acid value per hour were measured, and the results are shown in Table 10.

For comparison, the procedure of Example 42 was repeated except that lithium bromide was not added (Comparative Example 7). The results are also shown in Table 10.

TABLE 10

| Run No. | Amount of cobalt acetate (mmoles) | Amount of cobalt bromide (mmoles) | Amount of lithium bromide (mmoles) | Combustion ratio | Increase of acid value per hour (mg KOH/g.hr) | Final acid value (mg KOH/g) |
|---|---|---|---|---|---|---|
| Example 42 | 2.7 | 0 | 3.0 | 5.6 | 73 | 218 |
| Example 43 | 1.35 | 1.35 | 0 | 5.8 | 73 | 220 |
| Comparative Example 7 | 2.7 | 0 | 0 | 17.4 | 67 | 201 |

EXAMPLE 44

In a 500 cc titanium autoclave equipped with a reflux condenser, stirrer, gas blow inlet, material feed inlet, a catalyst solution feed inlet and reaction mixture outlet, mirror surface-finished test pieces (made of SUS 316 and SUS 304 stainless steels) having surface area of 27 cm$^2$ were fitted at a position at which two-thirds of the test pieces were immersed in the liquid phase. The autoclave was charged with 87.5 g of PX, 162.5 g of MPT, 5 g of PTA, 1.078 g (4.33 mmoles; 1000 ppm as Co in the starting mixture fed) of cobalt acetate tetrahydrate, 0.228 g (0.93 mmole; 200 ppm as Mn in the starting mixture fed) of manganese acetate tetrahydrate and 0.985 g (9.75 mmoles; 3000 ppm as Br in the starting mixture fed) of sodium bromide. Air was blown into the autoclave so that the flow rate of the exhaust gas became 1000 cc/min. (atmospheric pressure). The reaction was started at a temperature of 170° C. and a pressure of 5 kg/cm$^2$·G. In this manner, the batchwise reaction was continued for 2 hours. Then, a mixture of PX and MPT (weight ratio 35:65) was fed continuously into the autoclave at a rate of 80 g/hour from the material feed inlet. Likewise, an aqueous solution containing cobalt acetate, manganese acetate and sodium bromide in a concentration of 1.33, 0.27, and 4.00% by weight respectively as Co, Mn and Br was fed continuously from the catalyst solution feed inlet at a rate of 6.0 g/hour. From the reaction mixture outlet, a part of the reaction mixture was withdrawn every 10 to 15 minutes to maintain the liquid level in the reactor constant. After a steady state was reached, the reaction mixture had an acid value of about 250 mg KOH/g.

After performing this continuous oxidation reaction for 60 hours, the test pieces were removed, and the rate of weight loss of the test pieces (mdd) was measured. The surfaces of these test pieces were also examined by a microscope for the presence of localized corrosion. The results are shown in Table 11.

TABLE 11

| Test piece | Rate of weight loss (mg/dm$^2$ · day) | Result of the microscopic examination |
|---|---|---|
| SUS 316 stainless steel | 18 | No change was noted. |
| SUS 304 stainless steel | 27 | Corrosion was noted. |

What we claim is:

1. A process for preparing an oxidation reaction mixture containing benzenecarboxylic acids, the content of the resulting terephthalic acid in said reaction mixture not exceeding 45% by weight, based on the total weight of the reaction mixture, which comprises oxidizing at least one aromatic hydrocarbon selected from the group consisting of p-xylene, p-toluic acid and methyl p-toluate with a molecular oxygen-containing gas in the liquid phase in the substantial absence of a lower aliphatic carboxylic acid as a solvent, said oxidation reaction being carried out in the presence of, as a catalyst, (A) a cobalt compound soluble in the reaction system
(B) a manganese compound soluble in the reaction system, and
(C) a bromine compound soluble in the reaction system; wherein the cobalt compound (A) and the manganese compound (B) are present in such a ratio and a concentration, calculated as cobalt metal and manganese metal, that
  (1) the cobalt metal/manganese metal atomic ratio is from 99.50/0.5 to 50/50, and
  (2) the total concentration of the cobalt metal and the manganese metal in the oxidation reaction system is from 150 ppm to 5,000 ppm, wherein the bromine compound (C) is present in the oxidation reaction system in such a ratio and a concentration, calculated as bromine, that
  (3) the atomic ratio of bromine/cobalt metal+manganese metal does not exceed 1.5/1, and
  (4) the total concentration of bromine in the oxidation reaction system is from 50 to 2,500 ppm.

2. A process according to claim 1 for preparing benzene-carboxylic acids which comprises oxidizing at least one aromatic hydrocarbon selected from the group consisting of p-xylene, p-toluic acid and methyl p-toluate with molecular oxygen-containing gas in the liquid phase in the substantial absence of a lower aliphatic carboxylic acid as a solvent, said oxidation reaction being carried out in the presence of, said catalyst which further comprises:

(D) an alkali metal compound soluble in the reaction system.

3. The process of claim 1 or 2 wherein the cobalt compound (A) and the manganese compound (B) are present in such a ratio and a concentration, calculated as cobalt metal and manganese metal, that
  (1) the cobalt metal/manganese metal atomic ratio is from 99.3/0.7 to 60/40, and
  (2) the total concentration of the cobalt metal and manganese metal in the oxidation reaction system is from 200 ppm to 3,000 ppm.

4. The process of claim 2 wherein the total concentration of the alkali metal compound (D), calculated as alkali metal, in the oxidation reaction system does not exceed 2,500 ppm.

5. The process of claim 2 wherein the total concentration of the alkali metal compound (D), calculated as alkali metal, in the oxidation reaction system is from 5 ppm to 1,500 ppm.

6. The process of claim 2 wherein the alkali metal compound is a compound of sodium, potassium or lithium.

7. The process of claim 2 wherein the alkali metal compound is a compound of sodium or lithium.

8. The process of claim 1 or 2 wherein the oxidation reaction is carried out at a temperature of from 150° C. to 220° C.

9. The process of claim 1 or 2 wherein the oxidation reaction is carried out at a temperature of from 160° C. to 210° C.

10. The process of claim 1 or 2 wherein the aromatic hydrocarbon is p-xylene.

11. The process of claim 1 or 2 wherein the aromatic hydrocarbon is a mixture of p-xylene and methyl p-toluate.

12. The process of claim 8 wherein the oxidation reaction is carried out at a reaction pressure which is sufficient to maintain the oxidation reaction system in the liquid phase and within the range of from atmospheric pressure to about 50 kg/cm$^2$.

13. The process of claim 12 wherein the partial pressure of oxygen is within the range of from about 0.2 kg/cm$^2$ to 10 kg/cm$^2$.

14. The process of claim 12 wherein the partial pressure of oxygen is within the range of from about 0.4 kg/cm$^2$ to 5 kg/cm$^2$.

15. The process of claim 2 wherein the cobalt compound (A) and the manganese compound (B) are present in such a ratio and a concentration, calculated as cobalt metal and manganese metal, that
  (1) the cobalt metal/manganese metal atomic ratio is from 99.30/0.7 to 60/40, and
  (2) the total concentration of the cobalt metal and manganese metal in the oxidation reaction system is from 200 ppm to 3,000 ppm; the bromine compound (C) is present in the oxidation reaction system in such a ratio and a concentration, calculated as bromine, that
  (3) the atomic ratio of bromine/cobalt metal+manganese metal does not exceed 1.5/1, and
  (4) the concentration of bromine in the oxidation reaction system is from 50 ppm to 2,500 ppm; the total concentration of the alkali metal compound (D), calculated as alkali metal, in the oxidation reaction system is from 5 ppm to 1,500 ppm and is a compound of sodium, potassium or lithium.

16. The process of claim 15 wherein the oxidation reaction is carried out with a temperature of from 150° C. to 220° C. and at a pressure of from atmospheric pressure to about 50 kg/cm$^2$.

17. The process of claim 12 wherein the aromatic hydrocarbon is p-xylene or a mixture of p-xylene and methyl p-toluate.

18. The process of claim 16 wherein the aromatic hydrocarbon is p-xylene or a mixture of p-xylene and methyl p-toluate.

* * * * *